United States Patent [19]

Larkin

[11] 4,364,387

[45] Dec. 21, 1982

[54] CONNECTING DEVICE FOR MEDICAL LIQUID CONTAINERS

[75] Inventor: Mark E. Larkin, Lindenhurst, Ill.

[73] Assignee: Abbott Laboratories, North Chicago, Ill.

[21] Appl. No.: 217,870

[22] Filed: Dec. 18, 1980

[51] Int. Cl.³ .............................................. A61M 5/14
[52] U.S. Cl. .............................. 128/214 C; 128/214.2; 128/272.3; 222/83
[58] Field of Search ........... 128/214 R, 214 C, 214 G, 128/214.2, 214.4, 221, 347, 272, 272.3; 222/80, 81, 83; 137/318; 285/39

[56] References Cited

U.S. PATENT DOCUMENTS

| | | | |
|---|---|---|---|
| 2,670,740 | 3/1954 | Beacham | 128/214 |
| 2,716,982 | 9/1955 | Ryan | 128/214 |
| 2,829,643 | 4/1958 | Debaz | 128/218 R |
| 2,915,062 | 12/1959 | Butler et al. | 128/214 |
| 3,039,468 | 6/1962 | Price | 128/347 |
| 3,306,563 | 2/1967 | Soto | 222/81 |
| 3,323,523 | 6/1967 | Scislowicz et al. | 128/214.4 |
| 3,786,811 | 1/1974 | Holbrook | 128/218 P |
| 3,941,171 | 3/1976 | Ogle | 141/309 |
| 4,161,177 | 7/1979 | Fuchs | 128/214.4 |
| 4,170,994 | 10/1979 | Komatsu | 128/214 C |
| 4,201,406 | 5/1980 | Dennehey et al. | 285/3 |
| 4,203,443 | 5/1980 | Genese | 128/272.3 |

FOREIGN PATENT DOCUMENTS 1088541 9/1954 France ............................ 222/83

*Primary Examiner*—Dalton L. Truluck
*Attorney, Agent, or Firm*—Robert S. Beiser; Robert L. Niblack

[57] ABSTRACT

An improved connecting device for medical liquid containers comprises an elongated tubular member having a lumen extending therethrough. Pivotable finger tabs are hingedly attached to and extend from the elongate tubular member, adapted for engagement with the fingers so as to facilitate application of the device to the liquid container. The finger tabs are pivotable in order to allow folding of the tabs against the elongate tubular member in a first position or selective extension of the tabs to a position perpendicular from the tubular member prior to use. The tabs are thereby compactly stored so that when a bag, such as a peritoneal dialysis or irrigation bag must be carried by the patient, the tabs are not in an extended position which would cause discomfort to the patient.

17 Claims, 12 Drawing Figures

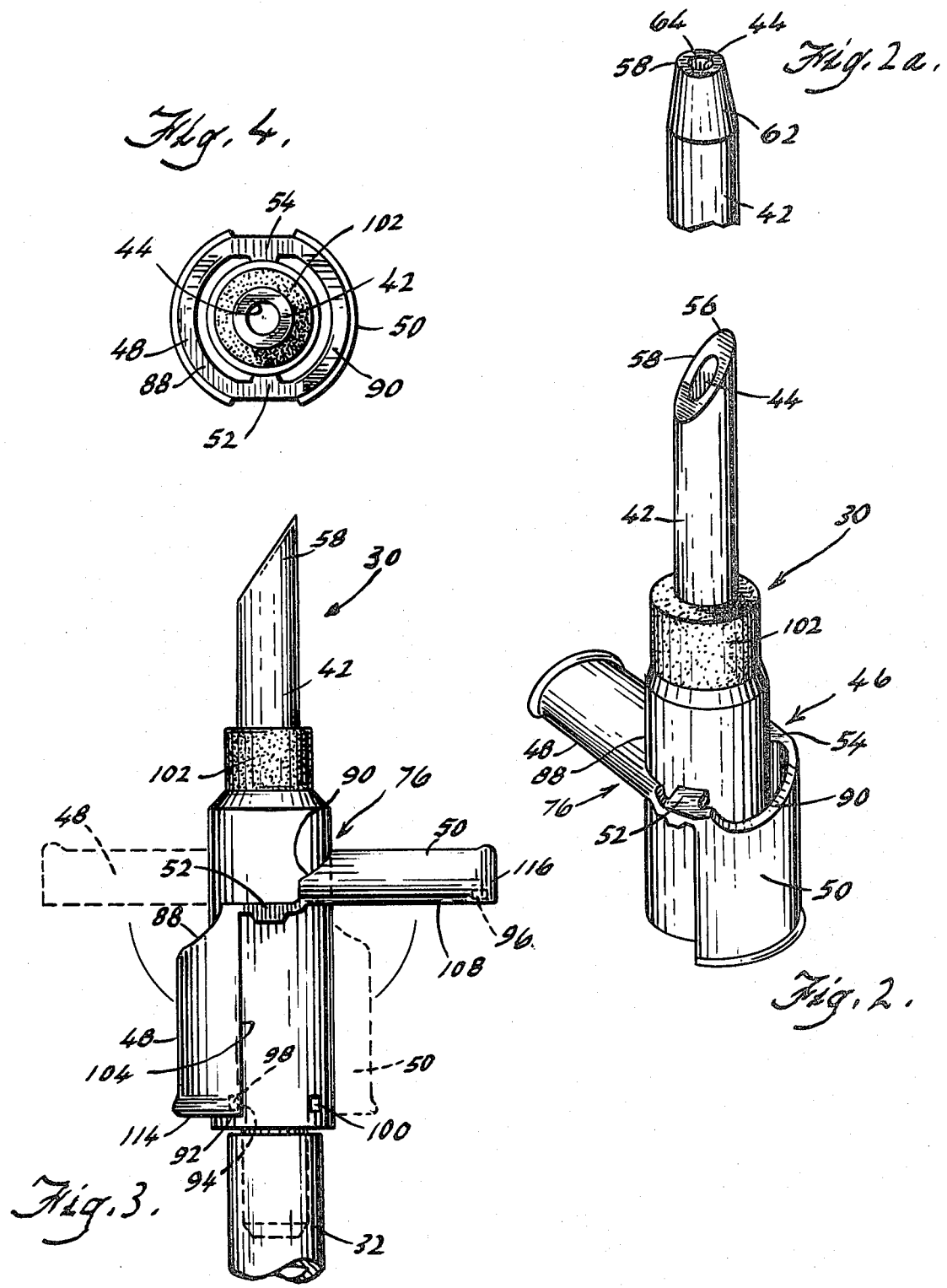

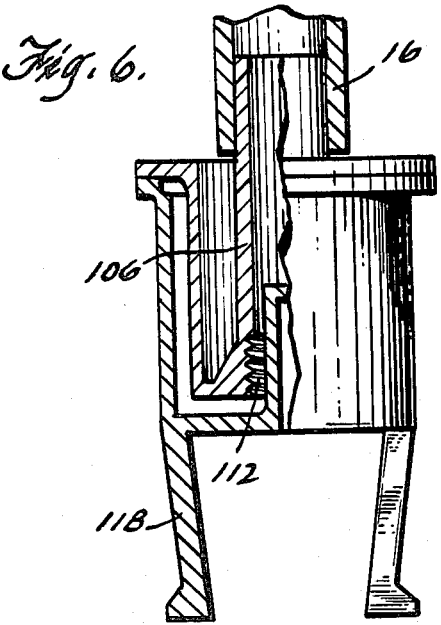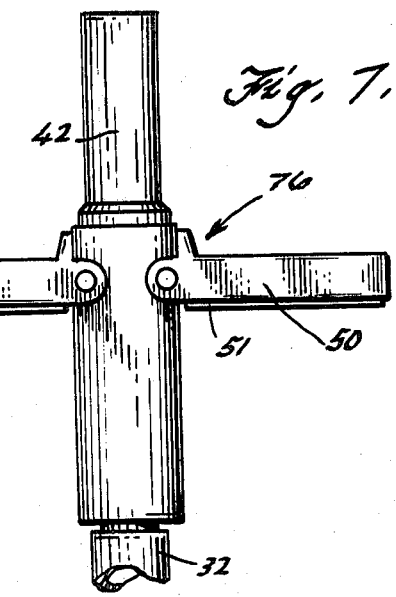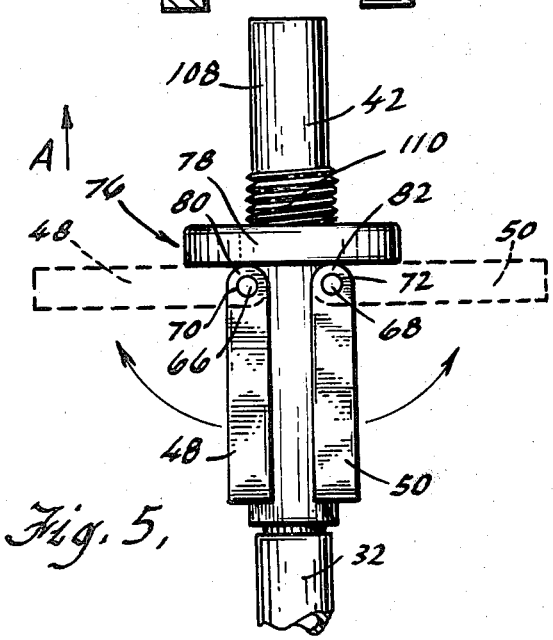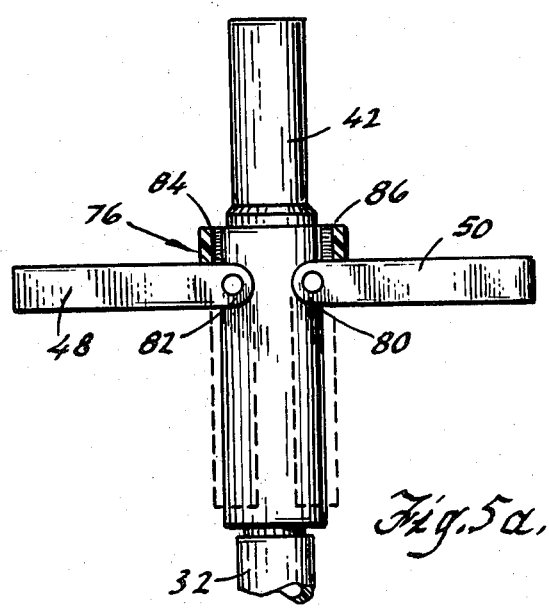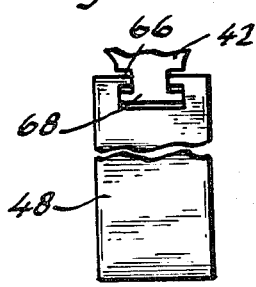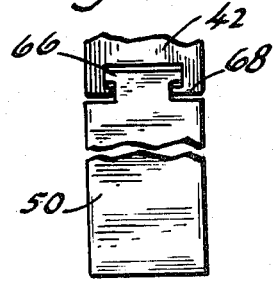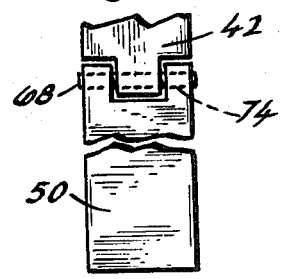

CONNECTING DEVICE FOR MEDICAL LIQUID CONTAINERS

BACKGROUND OF THE INVENTION

The present invention relates generally to systems and equipment for the adminstration of medical liquids to a patient, and more particularly to piercing pins and tubular connectors used to create a fluid pathway from a medical liquid container such as those utilized in continuous ambulatory peritoneal dialysis.

The parenteral and peritoneal administration of medical liquids to patients is a long established practice. Liquids, including amino acids, blood, dextrose, electrolytes and saline are commonly administered to patients over prolonged periods of time. Similarly, recent innovations in dialysis have resulted in the use of peritoneal adminstration of dialysate solution to patients. Generally, these liquids are administered from a glass bottle or plastic bag suspended abbove the patient, containing from 250 to 2,000 ml. of the liquid.

Medical liquid containers typically have an outlet port extending therefrom with the port having a diaphragm adapted for penetration by a piercing pin or spike from a tubing set. When the piercing pin is inserted through the diaphragm, medical liquid flows from the container, through the piercing pin, and by means of the tubing set, into the patient.

It is frequently a necessity that the sterility of the system be maintained when utilizing sterile medical liquids. In particular, in peritoneal dialysis, a dialysate solution is introduced into a patient's peritoneal cavity and is thereafter drained from the peritoneal cavity to the original solution container or elsewhere. In continuous ambulatory peritoneal dialysis, a plastic container of dialysate solution is connected to tubing, which is coupled to a catheter leading to the patient's peritoneum. The dialysate solution within the flexible container is administered through the tubing into the patient's peritoneum, following which the tubing is clamped and the solution bag folded and carried by the patient for several hours while the dialysate solution remains in the peritoneum. After about three or four hours, the solution bag is unfolded, the tubing unclamped and the solution within the peritoneal cavity drained into the same solution bag. Thereafter, the tubing is removed from the solution bag and is connected to a fresh solution bag, whereupon the procedure is repeated. It is therefore particularly apparent that by reducing the size of the connecting mechanism between the tubing and the liquid container, the patient may more comfortably fold the container and carry it with him. At the same time, it is imperative that accidental contact between the patient's fingers and the piercing pin be prevented in order to insure sterility of the system and the prevention of peritonitis.

It is therefore an advantage of the present invention to provide a connecting mechanism which is foldable, so as to reduce the size and bulk. It is an additional advantage of the present invention to provide a connecting mechanism that prevents accidental touch contact between the patient and the connecting mechanism in order to prevent contamination of the connecting mechanism and consequent infection of the patient.

SUMMARY OF THE INVENTION

The present invention comprises an improved connecting device for liquid containers. An elongate tubular member such as a piercing pin has a lumen or longitudinal passage extending therethrough. Attached to the elongate tubular member are, in a preferred embodiment, a pair of pivotable finger tabs hingedly attached to and extending from the tubular member. The tabs are designed for engagement with the fingers of the user in order to facilitate manipulation of the device and to prevent contact between the fingers of the user and the tubular member. The finger tabs are constructed so as to be aligned against the elongated tubular member in a first position and extend outward into a substantially perpendicular configuration in a second position. The first position is designed for compact storage and the second position is designed for digital engagement.

In a preferred embodiment, the elongated tubular member is a piercing pin having a sharpened tip at its distal end. The piercing pin is designed for penetrating and extending into a pierceable liquid container, particular by a medical container. A port, or ports, are positioned at the distal end of the piercing pin and open into a lumen which extends through the piercing pin, in order to allow the flow of liquid therethrough.

In a preferred embodiment of the invention, the pivotable finger tabs are integrally formed from and attached to the elongated tubular member by means of a flexible or living hinge extending between the tubular member and the finger tabs. In a preferred embodiment, the elongated tubular member includes a tubular sleeve concentrically disposed thereabout and attached thereto, having a plurality of hinges and pivotable finger tabs extending therefrom. As a result, a modular unit is provided having the pivotal finger tabs extending therefrom. Alternatively, the finger tabs may extend directly from the elongated tubular member when it is constructed of a material which is flexible in thin gauges. As an additional alternative, each finger tab may have a pivoting pin position proximate the proximal portion thereof and attached to the elongated tubular member. The pivoting pins may extend from the elongated tubular member, the sleeve, or the finger tabs, as long as they pivotally connect to the opposing member. The pivoting pins facilitate arcuate movement of the finger tabs either against the elongated tubular member or extending perpendicularly therefrom.

In a preferred embodiment, the finger tabs include a stop mechanism operatively associated therewith which rigidly fix the finger tabs in an open configuration when required. As a result, when force is applied against the finger tabs by the fingers of the user, the force may be directed through the elongated tubular member to help pierce the path of the medical liquid container. The stop mechanism comprises a collar integrally formed on the elongated tubular member and abutting the proximal end of the finger tabs. The collar is constructed to limit the arcuate opening movement of the finger tabs to a substantially perpendicular position from the elongated tubular member so that when the finger tabs are directed against the collar, force is applied to the collar and thereby against the connector device so as to force it into the liquid container.

Alternatively, a series of shoulders may be positioned proximate the proximal end of the finger tabs to limit the extension of the finger tabs to a substantially perpendicular position.

In an alternative embodiment, the stop mechanism comprises a curved indent in each finger tab proximate the proximal portion thereof. The curved indents are shaped for mating interfitment with the elongated tubular member. Disposed on each side of the curved indents are hinge mechanism connected to the elongate tubular member which allows the finger tabs to be pivoted. The curve indents are constructed and arranged so as to limit the pivoting motion of the hinges to a full extension or perpendicular position from the elongate tubular member.

As an additional feature of the invention, the pivotable finger tabs may further include a detent or latch mechanisms for selectively engaging the distal ends of the finger tabs against the elongated tubular member while the device is being stored or carried. When the use of the finger tabs is desired, the detent mechanisms are released. The finger tabs may further include cushions integrally formed therein in order to enhance user comfort in the application of pressure against the finger tabs.

As an additional feature of the invention, the elongated tubular member may include an antiseptic carrier circumscribing portions thereof which squeezably releases an antiseptic solution at the juncture between the connecting device and the liquid container in order to asepticize said connection. The antiseptic carrier preferably comprises a sponge having an antiseptic solution such as povidone iodine contained therein. In a preferred embodiment, the liquid container includes a sealed tubular port of the proper inside diameter and length to telescopically engage with and attach to the connector device. The elongated tubular member preferably has an outside diameter slightly smaller than the tubular port so as to permit such telescopic engagement and a press-fit connection therein.

As an additional alternative, the elongated tubular member may include a series of concentric threads disposed thereon adapted for engagement with a corresponding series of mating threads within the tubular port. In this and other embodiments, the tubular port may have a graduated inside diameter with the innermost portion being substantially the same size as the elongated tubular member and the outermost portion being substantially the same size as the finger tab mechanisms. As a result, when the connector mechanism is inserted into the port, the outer portion of the port will fold the finger tabs downward against the connecting device so as to receive the entire connecting mechanism therein and to releasably engage same.

BRIEF DESCRIPTION OF THE DRAWINGS

FIG. 2 of the drawings is a front perspective view of an improved connector device used in the medical liquid administration set of FIG. 1.

FIG. 2A of the drawings is a partial front perspective view of an alternative embodiment of the connector device of FIG. 2.

FIG. 3 of the drawings is a front view of the connector device of FIG. 2.

FIG. 4 of the drawings is a top view of the connector device of FIG. 3.

FIG. 5 of the drawings is a front view of an alternative embodiment of the connecting device of FIG. 2.

FIG. 5a of the drawings is a front view of an alternative embodiment of the connecting device of FIG. 5 partially broken away.

FIG. 6 of the drawings is a front view, partially broken away, of an alternative embodiment of the tubular port extending from the liquid container of FIG. 1.

FIG. 7 of the drawings is a front view of an alternative embodiment of the connecting device of FIG. 5.

FIGS. 8a-c of the drawings are front views of a series of alternative methods of connecting the pivotable finger tabs to the device of FIG. 7.

DETAILED DESCRIPTION OF THE PREFERRED EMBODIMENT

Figure 1:
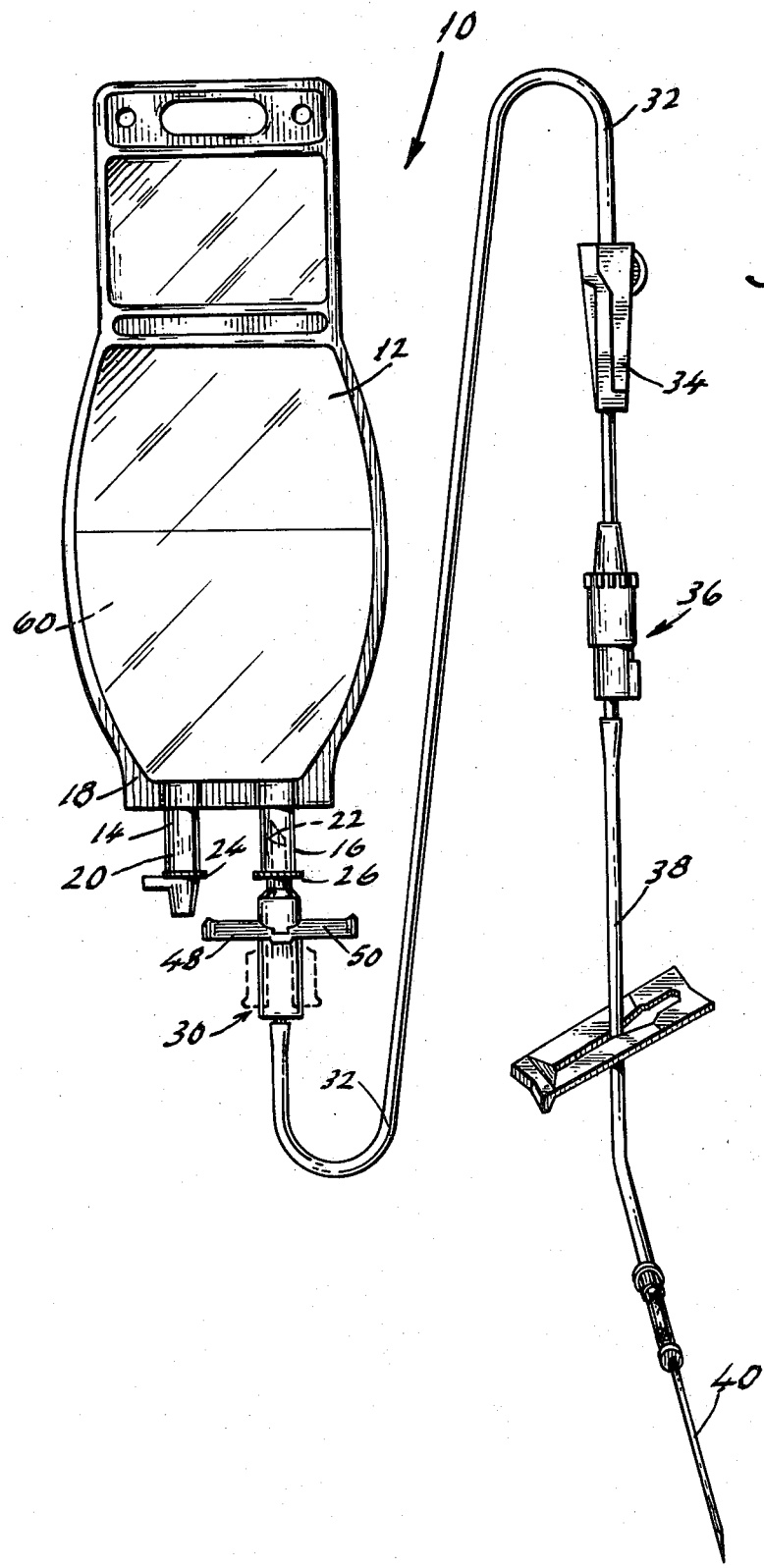
FIG. 1 of the drawings is a front view of a medical liquid administration set particularly adapted for performing continuous ambulatory peritoneal dialysis.

While this invention is susceptible of embodiment in many different forms, there is shown in the drawings and will herein be described in detail, several specific embodiments with the understanding that the embodiments illustrated are to be considered as an exemplification of the principles of the invention and are not intended to limit the invention to the embodiments illustrated.

Referring to FIG. 1, a conventional medical liquid administration set 10 is shown therein, including a medical liquid container 12, having ports 14 and 16 extending from end 18 of container 12. As shown, ports 14 and 16 have axial bores 20 and 22 extending therethrough and transverse diaphragms 24 and 26 which block fluid flow from the container until the diaphragm is broken.

Although liquid container 12 is illustrated as a flexible bag, it is understood that the instant invention is applicable to rigid containers such as glass bottles, and also to various types of medical procedures including, but not limited to, continuous ambulatory peritoneal dialysis.

As further illustrated in FIG. 1 of the drawings, medical liquid administration set 10 further includes connecting device 30 inserted into port 16 and having flexible tubing 32 extending therefrom. Roller clamp 34 selectively controls the rate of flow of liquid from container 12 through tubing 32. At the distal end of tubing 32 is quick disconnect 36 which is further connected to flexible tubing 38. Flexible tubing 38 is connected at its distal end to catheter 40, which in peritoneal dialysis, is inserted into the peritoneum of the patient. Thus, liquid may selectively flow either through tubing 32 and 38 into the peritoneum of the patient or conversely, be drained therefrom.

As best seen in FIG. 2 of the drawings, improved connector device 30 comprises an elongated tubular member 42, having a longitudinal fluid passage or lumen 44 extending therethrough. Hingedly attached to and extending from elongated tubular member is pivotable finger tab mechanism 46. As shown, pivotable finger tab mechanism 46 comprises a pair of finger tab members 48 and 50 constructed and arranged for engagement with the fingers of the user, thereby facilitating manipulation of the connecting device 30. Hinge mechanisms 52 and 54 allow finger tab members 48 and 50 to be aligned against tubular member 42 in a first position and to be extended into a substantially perpendicular configuration in a second position. The first position is adapted for compact storage of the finger tabs, and the second position is adapted for gripping by the user when inserting connector 30 into port 16 of container 12.

As further seen in FIG. 2, in a preferred embodiment, elongated tubular member 42 comprises a piercing pin having a sharpened tip 56 at its distal end 58 constructed and arranged for penetration of diaphragm 26 and extension into port 16 extending from liquid container 12.

Once such penetration is effective, liquid 60 may flow from container 12, through port 16, connecting device 30, flexible tubing 32 and 38, catheter 40, and into the patient.

As further seen in FIGS. 2 and 3, pivotable finger tabs 48 and 50 are attached to tubular member 42 by means of flexible hinges 52 and 54 extending from elongated tubular member 42. Hinges 52 and 54 are constructed of a plastic material sufficiently elastic and of a sufficient thickness to allow multiple flexures of the hinges, such as polypropylene, while at the same time being sufficiently thick and resilient to resist cracking or breaking. As indicated seen in FIGS. 2 and 3, connecting device 30 may include a tubular sleeve 60 concentrically disposed about and attached to elongated tubular member 42. Tubular sleeve 60 has flexible hinge mechanism 46 (and thereby pivotable finger tabs 48 and 50) integrally formed and extending therefrom, so as to provide a modular connecting mechanism comprising elongated tubular member 42, sleeve 60 and finger tabs 48 and 50.

As best seen in FIG. 2A, in one embodiment of the invention, elongated tubular member 42 has a frustoconical tip 62 at its distal end 58 with a port 64 disposed thereon and opening into longitudinal lumen 44. Frustoconical tip 62 is utilized in medical liquid containers in which the piercing of a diaphragm is not required.

Referring to FIG. 5 of the drawings, an alternative embodiment is described having pivotable finger tabs 48 and 50 which may include pivoting pins 66 and 68 connecting tabs 48 and 50 to elongated tubular member 42, or alternatively, tubular sleeve 60. As shown, pivoting pins 66 and 68 are rotatably mounted within circular apertures 70 and 72 integrally formed in tabs 48 and 50. However, as seen in FIGS. 8A and 8B, pivoting pins 66 and 68 may be integrally formed on tab 48 and extend inwardly or outwardly as required. Alternatively, as seen in FIG. 8C, pivoting pins 68 and 66 may comprise separate metal or plastic pins inserted through opening 74 which extends through tab 50. As a result of the connection between pivoting pins 66 and 68 and elongated tubular member 42, flexible tabs 48 and 50 may be pivoted in an arcuate movement against elongated tubular member 42 or extending perpendicularly therefrom.

As seen in FIGS. 2, 3, 5 and 7, operatively associated with finger tabs 48 and 50 is stop mechanism 76. As seen in FIG. 5, stop mechanism 76 comprises a collar 78 integrally formed on elongated tubular member 42 abutting the proximal ends 80 and 82 of finger tabs 48 and 50. Collar member 78 is of a proper size and configuration to limit the arcuate opening movement of finger tabs 48 and 50 to a substantially perpendicular position from tubular member 42. As a result, when digital force applied is against finger tabs 48 and 50 in direction A, force is transmitted against collar 78 and thereby against connector device 30 in direction A. Connector 30 may thereby be forced into port 16, as best seen in FIG. 1. Alternatively, as best seen in FIG. 5A, stop means 76 may comprise shoulders 84 and 86 extending from elongated tubular member 42 and abutting proximal ends 80 and 82 of tabs 48 and 50. Shoulders 84 and 86 limit the extension of finger tabs 48 and 50 to a substantially perpendicular position.

Returning to FIGS. 2 and 3, in a preferred embodiment, stop means 76 comprises curvelinear or curved indents 88 and 90 proximate the proximal ends 80 and 82 of finger tabs 48 and 50. Curved indents 88 and 90 are shaped and positioned for mating interfitment with elongated tubular member 42. As finger tabs 48 and 50 are pivoted on hinges 52 and 54, curved indents 88 and 90 mate into and are stopped by tubular member 42, leaving finger tabs 48 and 50 in a substantially perpendicular position from tubular member 42. Indents 88 and 90 are intermediate, (disposed between) hinges 52 and 54 in order to allow such pivotable mating engagement.

As further seen in FIG. 3, connecting device 30 may include detent mechanism 92 and 94, for releasably engaging finger tabs 48 and 50 against elongated tubular member 42 in the closed first position previously described. In a preferred embodiment, detent mechanism 92 comprises resilient prongs 94 and 96 extending perpendicularly from the distal ends of finger tabs 48 and 50 and positioned for engagement into apertures 98 and 100 on sleeve 60. As finger tabs 48 and 50 are closed against tubular member 42, prongs 94 and 96 are snap-fit into apertures 98 and 100, thereby releasably holding finger tabs 48 an 50 in a closed configuration.

As seen in FIG. 7, finger tabs 48 and 50 may be constructed of a relatively soft cushioning material on their ventral surface so as to facilitate user comfort. Alternatively, one or more pads 49 and 51 may be disposed on the ventral surface of finger tabs 48 and 50 to enhance such user comfort.

As best seen in FIG. 3 of the drawings, in a preferred embodiment, connecting device 30 includes an antiseptic carrier 102 telescopically disposed on tubular member 42 proximate distal end 58, which is of the proper size so as to abut against port 16 when connector mechanism 30 is joined thereto. In a preferred embodiment, antiseptic carrier 102 comprises a resilient sponge containing an antiseptic solution which compresses against port 16, thereby releasing antiseptic solution so as to aseptize the connection.

As best seen in FIG. 6 of the drawings, liquid container 12 may include a sealed tubular port 16 having an inside diameter 106 substantially the same size as the outside diameter 108 of elongated tubular member 42. When the elongated tubular member 42 of FIG. 5 is inserted into port 16, a press-fit connection between Outside Diameter 108 and Inside Diameter 106 is created.

As further seen in FIGS. 5 and 6 of the drawings, elongated tubular member 42 may include a series of helical threads 110 disposed thereabout and adapted for rotational engagement with the corresponding series of mating threads 112 in port 16. Thus, once initial penetration of piercing pin 56 or rounded top 62 is accomplished, rotation of elongated tubular member 42 causes threading 110 to slidably advance in port 16 until a seal is effected.

Tubular port 16 includes tubular collar 118 extending therefrom. Tubular collar 118 is adapted for folding finger tabs 48 and 50 against elongated tubular member 42 as connecting device 30 is inserted into port 16. As a result, connecting device 30 may be compactly retained in port 16 following connection.

Returning to FIG. 3 of the drawings, in a preferred embodiment, finger tabs 48 and 50 are adapted for the application of digital force against ventral surfaces 104 and 108 and against distal ends 114 and 116. As a result, connecting device 30 may be forced into tubular port 16 while finger tabs 48 and 50 are in either a folded or open position.

The foregoing description and drawings merely explain and illustrate the invention, and the invention is not limited thereto, except insofar as the appended claims are limited by those skilled in the art who have the disclosure before them and are able to make modifications and variations therein without departing from the scope of the invention.

I claim:

1. An improved connector device for liquid containers having a tubular port extending therefrom comprising:
   an elongated tubular member having means constructed and arranged for telescopic connection to said tubular port;
   at least one longitudinal fluid passage extending through said tubular member for the passage of liquid, the improvement comprising:
   pivotable finger tabs means hingedly attached to and extending from said elongated tubular member for the digital engagement and manipulation of said connector, said pivotable finger tab means having means constructed and arranged for selective coaxial alignment against said elongated member in a first position and for arcuate extension into locking fixation in a substantially normal configuration in a second position, thereby facilitating storage in said first position and digital engagement and manipulation of said connector in said second position.

2. The connector device as disclosed in claim 1 wherein said elongated tubular member comprises:
   a piercing pin having a sharpened tip at its distal end constructed and arranged for penetration of and extension into said tubular port of said liquid container; and
   one or more port members operatively associated with said longitudinal fluid passages constructed and arranged for the passage of liquid therethrough.

3. A piercing pin for medical liquid administration sets including a medical liquid container having a penetrable sealing member at a first end, said piercing pin comprising:
   an elongated tubular member having a sharpened tip at its distal end and at least one longitudinal fluid passage extending therethrough, the improvement comprising:
   pivotable finger tap means hingedly attached to and extending from said elongated tubular member, for the digital engagement and manipulation of said connector, said pivotable finger tab means being constructed and arranged for selective alignment against said elongated tubular member in a first position and for arcuate extension into and locking fixation in a substantially normal configuration in a second position, thereby facilitating storage in said first position and digital engagement and manipulation in said second position.

4. The connector device as disclosed in claim 1 wherein said pivotable finger tab means are integrally formed from and attached to said elongated tubular member by means of a plurality of flexible hinge members extending therebetween, said hinge members being constructed of a plastic material sufficiently elastic and being of a sufficient thickness to allow multiple flexures of said hinge while at the same time being sufficiently thick and resilient so as to resist cracking or breaking therefrom.

5. The connector device as disclosed in claim 4 wherein said connector device further comprises a tubular sleeve member concentrically disposed about and attached to said elongate tubular member, said sleeve member having said flexible hinge means and said pivotable finger tab means integrally formed and extending therefrom, so as to provide a modular connector mechanism having said pivotable finger tab means extending therefrom.

6. The connector device as disclosed in claim 1 wherein said pivotable finger tab means comprises a plurality of pivoting pins pivotably attached to the proximal portion of said plurality of finger tab members and attached to said elongate tubular member, said pivoting pins being constructed and arranged for facilitating the accurate movement of said finger tab members selectively against said elongate tubular member or extending therefrom.

7. The connector device as disclosed in claim 1 wherein said finger tab means comprises stop means operatively associated therewith for rigidly fixing said finger tab means in an open configuration so a to facilitate the directional application of force against said elongate tubular members by means of digital pressure against said open finger tab means.

8. The connector device as disclosed in claim 7 wherein said stop means comprises a collar member integrally formed on said elongate tubular member and abutting the proximal ends of said finger tab means, said collar member being constructed and arranged to limit the arcuate opening movement of said finger tab means to a substantially normal position extending from said elongate tubular member whereby said digital pressure against said finger tab means is directed againt said collar member thereby forcing said connector device forward in the direction desired.

9. The connector device as disclosed in claim 7 wherein said stop means comprises,
   a plurality of shoulder members positioned proximate the proximal ends of said finger tab means, said shoulder members being constructed and arranged so as to limit the extension of said finger tab means to a substantially normal position.

10. The connector device as disclosed in claim 1 wherein said pivotable finger tab means further comprise,
    detent means for releasably engaging said finger tab means against said elongate tubular member in said first position.

11. The connector device as disclosed in claim 1 wherein said pivotable finger tab means further comprises cushion means operatively associated with said finger tab means for enhancing user comfort in application of digital pressure against said finger tab means.

12. The connecting device as disclosed in claim 10 wherein said detent means comprises
    a plurality of prong members attached to and extending from the ventral portion of said finger tab means; and disposed on said elongate tubular member and a plurality of mating apertures adapted for snap fit engagement with and selective retention of said prong members and thereby said finger tab means, as required.

13. The connector device as disclosed in claim 1 and further comprising antiseptic carrier means operatively associated with said elongate tubular member for substantial asepticization of the connection between said connector device and said liquid container.

14. An improved connector device for liquid containers having a tubular port extending therefrom comprising:

an elongated tubular member constructed and arranged for telescopic connection to said tubular port;

at least one longitudinal fluid passage extending through said tubular member for the passage of liquid, the improvement comprising:

pivotable finger tabs means hingedly attached to and extending from said elongated tubular member for the digital engagement and manipulation of said connector, said pivotable finger tab means being constructed and arranged for selective alignment against said elongated member in a first position and for arcuate extension into a substantially normal configuration in a second position, thereby facilitating storage in said first position and digital engagement and manipulation of said connector in said second position;

antiseptic carrier means operatively associated with said elongated tubular member for substantial aseptization of the connection between said connector device and said liquid container said antiseptic carrier means comprises a resilient tubular sponge member concentrically disposed about said elongated tubular member and containing antiseptic solution, said sponge member being constructed and arranged for compressive engagement against said liquid container so as to aseptically seal same.

15. An improved connector device for liquid containers comprising an elongated tubular member having at least one longitudinal fluid passage extending therethrough, pivotable finger tab means hingedly attached to and extending from said elongated tubular member for the digital engagement and manipulation of said connector, said pivotable tab means being constructed and arranged for selective alignment against said elongated tubular member in a first position and for arcuate extension into a substantially normal configuration in a second position, thereby facilitating storage in said first position and digital engagement and manipulation in said second position, said finger tab means including stop means operatively associated therewith for rigidly fixing said finger tab means in an open configuration so as to facilitate the directional application of force against said elongated tubular members by means of digital pressure against said open finger tab means, said stop means comprising a plurality of curvilinear indents integrally formed proximate the proximal portion of said finger tab means, constructed and arranged for mating interfitment with said elongated tubular member, said curvilinear indents being constructed and arranged so as limit, in cooperation with said hinge means, the extension of said finger tab means to a substantially normal position, said indents being intermediate said hinge means disposed on each side of said proximal portion of said finger tab means.

16. The connector device as disclosed in claim 1 or 14 wherein said finger tab means are constructed and arranged for the selective application of digital force against the distal ends thereof or alternatively against the ventral surface thereof.

17. The connector device as disclosed in claim 14 wherein elongate tubular member further includes a series of helical threads disposed thereon adapted for selective engagement with a corresponding series of mating threads within said tubular port member.

* * * * *